US007288551B1

(12) United States Patent
Masters

(10) Patent No.: US 7,288,551 B1
(45) Date of Patent: Oct. 30, 2007

(54) SOLUTION FOR THE PRESERVATION OF HEARTS

(75) Inventor: Thomas N. Masters, Charlotte, NC (US)

(73) Assignee: Charlotte-Mecklenburg Hospital Authority, Charlotte, NC (US)

( * ) Notice: Subject to any disclaimer, the term of this patent is extended or adjusted under 35 U.S.C. 154(b) by 326 days.

(21) Appl. No.: 10/088,538

(22) PCT Filed: Sep. 19, 2000

(86) PCT No.: PCT/US00/40939

§ 371 (c)(1),
(2), (4) Date: Jun. 10, 2002

(87) PCT Pub. No.: WO01/20982

PCT Pub. Date: Mar. 29, 2001

(51) Int. Cl.
*A61K 31/47* (2006.01)
*A01N 43/42* (2006.01)
(52) U.S. Cl. ....................... 514/311; 435/1.2
(58) Field of Classification Search .............. 514/11, 514/311; 424/600; 435/1.2
See application file for complete search history.

(56) References Cited

U.S. PATENT DOCUMENTS 5,665,774 A  9/1997 Armistead et al.
5,693,462 A * 12/1997 Raymond ............... 435/1
5,925,510 A  7/1999 Schulsinger

OTHER PUBLICATIONS

Juado et al, 129CA:239628, 1998.*
Massoudy et al, 126CA:338797, 1997.*
Massoudy et al. "Cardioprotection by Cyclosporine A in Experimental Ischemia and Reperfusion" 1997, J. Mol. Cell. Cardiol., 29, 535-544.*
Griffiths, E.J., Halestrap AP: Protection by cyclosporine A of ischemia/reperfusion-induced damage in isolated rat hearts, *J Mol Cell Cardiol*, (1993) 25:1461-1469.
Masters, T.N. et al.; "Extending myocardial viability during heart preservation with cyclosporine A."; Journal of Heart and Lung Transplantation, vol. 19, No. 1, Jan. 2000, p. 41.

* cited by examiner

*Primary Examiner*—Sreeni Padmanabhan
*Assistant Examiner*—Leonard Williams
(74) *Attorney, Agent, or Firm*—Alston & Bird LLP

(57) ABSTRACT

The present invention is directed to preservation solutions for storing and perfusing a heart intended for transplantation to a patient requiring such implant. It was found that when cyclosporin is added to the preservation solution for to: (1) preserve the mitochondrial function which it does by maintaining adenosine triphosphate ("ATP") levels, and (2) to block apoptosis and prevent programmed cell death. Therefore, the preservation of the mitochondrial function prevents necrosis while blocking prevents apoptosis.

8 Claims, 7 Drawing Sheets

SOLUTION FOR THE PRESERVATION OF HEARTS

BACKGROUND OF THE INVENTION (1) Field of the Invention

The present invention relates to solutions for the preservation of hearts. More particularly, this invention relates to preservation solutions for perfusing and storing a heart while awaiting transplantation, and to methods for using the preserving solution during transplantation of an organ.

(2) The Prior Art

Preservation of hearts awaiting transplantation has become common practice in many hospitals; however, the ability to make transplantations are limited to the viability of the heart. A great deal of progress has been made over the years in understanding cellular mechanisms, as well as developing new transplantation techniques for keeping organs viable, not only during storage, but also after reperfusion of these organs. As a result, organ transplantation including heart transplantation, is an established elective operation. A significant factor limiting the clinical application of organ transplantation is the deviation of viability for the organ after removal from the donor. Long term preservation of heart tissue results in two kinds of cell destruction: (1) necrosis and (2) apoptosis. Necrotic cell damage results in cell swelling with the cell organelles also swelling until the cell ruptures spilling its contents into the extra cellular space. Apoptosis (program cell death) is an organized destruction of the cell with the cellular components shrinking until nothing remains. During embryonic development, apoptosis plays an important role in tailoring various organs for adult use. Apoptosis is also present in ischemic (oxygen deprived) heart tissue as well as necrosis when preserved for 90 minutes at normal body temperatures. Apoptosis appears to be a more destructive mechanism to myocardial cells during ischemia.

The compositions of numerous of preservation solutions have been extensively studied. For example, the protective properties of cold preservation solutions was set forth in G. Tian, et al. (1991), the *Journal Of Heart And Lung Transplantation* (10) 975-985, where the cold preservation solutions limited the storage time of the organ. A preservation solution useful by all donor organs, both for in situ organ cooling in the donor and for cold storage after the organ is harvested is available from E.I. du Pont de Nemours and Co. under the trademark VIASPAN® and disclosed in U.S. Pat. No. 4,879,283. The solution of U.S. Pat. No. 4,879,283 has extended the preservation time of organs intended for transplantation, extending for example the viability of livers from 6 to 10 hours to over 24 hours. While the solution of U.S. Pat. No. 4,879,283 has been effective in extending the preservation time of organs intended for transplantation, cell injury still occurs. Therefore, a further reduction in cell injury and increased survival time is desirable. Another patented solution for the preservation of organs is U.S. Pat. No. 4,873,230 entitled "Composition For The Preservation Of Organs." Yet another patented solution is U.S. Pat. No. 4,798,824 entitled "Perfusate For The Preservation Of Organs" which discloses a hydroxyethyl starch composition useful in a preservation solution.

The introduction of cyclosporin for immunosuppression during the 1980's, revived interest in transplanted organs and tissues, specifically, the liver, kidneys, pancreas, heart and lung. However, preservation methods that were successful for kidneys have not proven for these other organs, such as hearts, because the heart is more complex to transplant than kidneys. Short preservation times for the heart also necessitate two surgical teams, one for the donor and the other for the recipient. Extending preservation times for the heart would have a positive impact on the transplantation, namely, increasing organ availability, decreasing organ wastage, including organ sharing and reducing costs. Cyclosporin, a drug used to prevent rejection, has also been reported to block apoptosis in certain cell systems.

Static storage versus continuous perfusion methods has shown large differences in the length of preservation. Metabolic changes during hypothermic storage are characterized by a loss of adenosine triphosphate (ATP) and creatine phosphate (CP) which lead to disruption of ion exchange pumps and electrolyte imbalances which intensify the cell damage and prevent heart recovery. Preservation of ATP and CP levels benefits long-term heart storage. However, at least 90% of the ATP is lost in most hypothermically stored organs within 2-4 hours, but fully recover after much longer periods of preservation.

One of the major criteria for heart transplantation, after proper matching procedures are met, is that the heart must be harvested from the donor, transported and re-implanted into the recipient within a four to six hour time frame. Although extended preservation times for hearts do not seem necessary, a more reliable preservation method may extend the ranges for which hearts can be transported and received. An 18 hour barrier has existed in most experimental laboratories for large mammalian hearts with a 50% functional recovery after six hours. Although not followed for longer periods of time, the six hour time frame was used because of its clinical relevance to the initial "new-heart" functional requirements which did not involve rejection and sterility issues. It was found that at 18 hours of preservation and 4° C. with University of Wisconsin (UW) solution, no necrosis was evident in a heart but apoptosis was present. Thus, if apoptosis can be blocked, the preservation times can be extended.

It is therefore the general object of this invention to delineate the relation of apoptotic and necrotic cell death to heart preservation.

Another object of the present invention is to determine if blocking apoptosis during heart preservation extends myocardial viability and push ahead the perceived limits of cold storage for hearts, allowing a greater time from donor harvest to recipient transplantation.

Still another object of the present invention to provide preservation solutions for pulsating and storing organs while awaiting implantation, which inhibits ion exchange, extends viability of the organ and reduces damage to the cell.

Yet another object of the present invention is to provide a method for preserving hearts which extends the maximum life of the heart during transplantation.

Other object features and advantages of the invention will be apparent from the following details of the invention as more fully described.

SUMMARY OF THE INVENTION

In accordance with these objects and the principles of this invention, there is disclosed a preservation solution for perfusing and storing a heart while awaiting transplantation, and methods for transplanting hearts using the preservation solutions, which methods increase storage times and are less injurious to the organ.

It has been found that a preservation solution containing cyclosporin preserves the mitochondrial function by maintaining ATP levels, and blocks apoptosis, thereby preventing programmed cell death. In a preferred embodiment of this invention, the preservation solution includes a balanced isotonic solution including sodium, potassium, calcium, magnesium ions and bicarbonate in a physiologically acceptable amount, from about 2.5 µM to about 10 µM of a cyclosporin, and water sufficient to make a liter of solution. Preferably from about 5.0 µM to about 7.0 µM of cyclosporin per liter of solution is used.

As the ischemic duration increases, tissue injury changes from a reversible to irreversible state. It has been shown that when ischemic myocardial tissue exhibits poly- (ADP-ribose) polymerase (PARP) fragments during normothermic preservation, reperfusion resulted in irreversible damage, characterized by the loss of functional ability and the appearance of apoptotic cells among numerous necrotic cells. When PARP fragments were not found, apoptosis was not seen upon reperfusion and myocardial irreversible damage was not found and functional recovery returned. In studies using 18-hour hypothermic preservation with UW solution, PARP fragments were found at the end of the 18-hour ischemic period and with reperfusion, apoptosis was found with no necrosis concomitant with a 50-60% return of LV function. The common pathway of necrosis and apoptosis via the mitochondrial permeability transition (MPT) pore suggests a possible mechanism that may limit myocardial preservation.

DETAILED DESCRIPTION OF THE INVENTION

Figure 1:
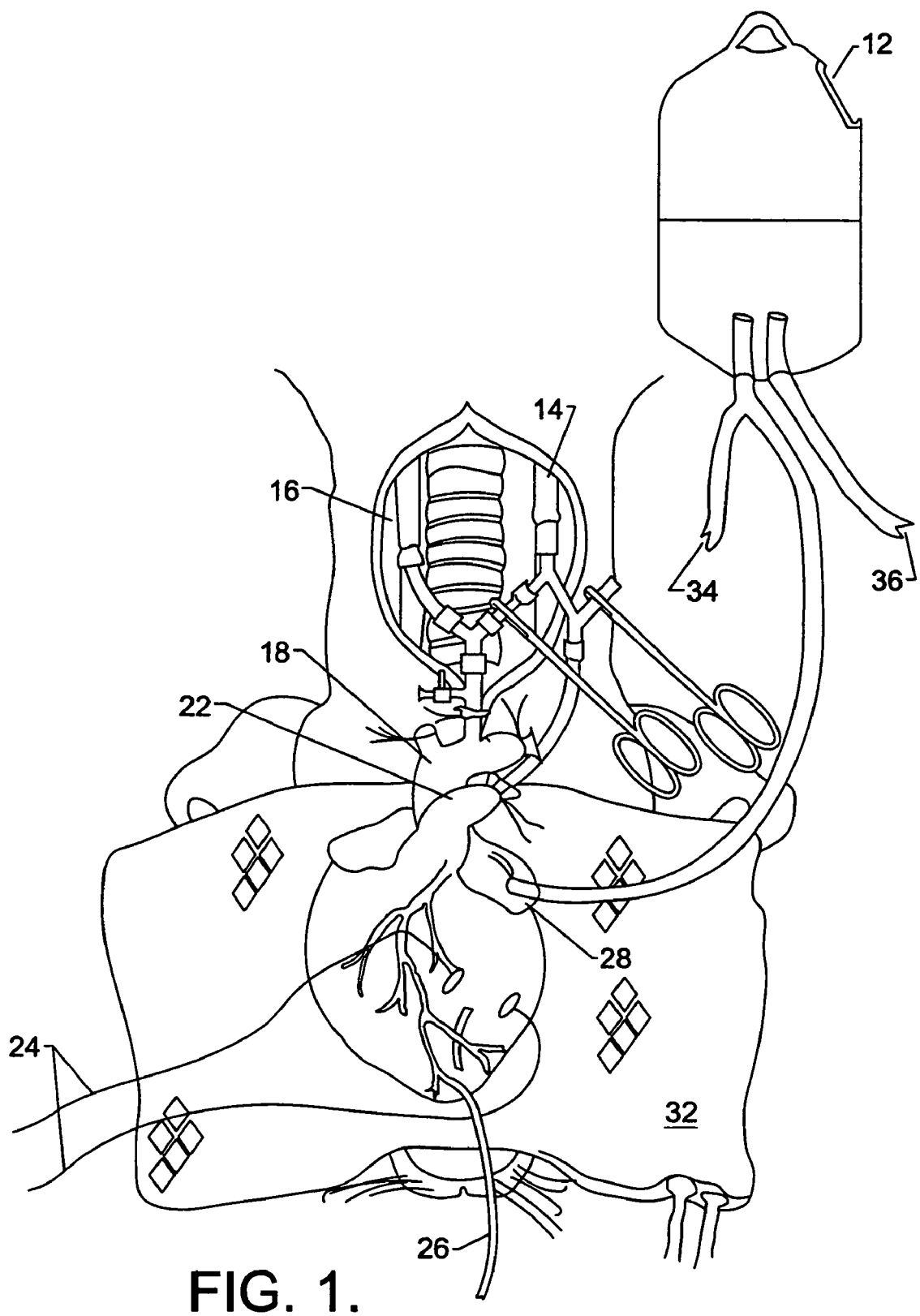
FIG. 1 is a diagrammatic representation of the heterotopic transplant procedure for donor heart reanimation and left ventricular (LV) function determination.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention is directed to preservation solutions for storing and perfusing a heart intended for transplantation to a patient requiring such implant. It was found that when cyclosporin is added to the preservation solution for to: (1) preserve the mitochondrial function which it does by maintaining adenosine triphosphate (ATP) levels, and (2) to block apoptosis and prevent programmed cell death. Therefore, the preservation of the mitochondrial function prevents necrosis while blocking prevents apoptosis.

The preservation solutions of this invention include a balanced isotonic solution in a physiological acceptable amount, a cyclosporin and the balance water. The preferred preservation solutions of the present invention are based on a balanced isotonic solution including sodium, potassium, calcium and magnesium ions as well as glucose and sodium bicarbonate in a physiologically acceptable amount. Certain of these types of solutions are well known, such as the one described below, known as Krebs-Henseleit-bicarbonate solution, which has the following composition:

TABLE 1

| Concentration Ranges in 1 Liter | |
|---|---|
| NaCl | 85 mM to 145 mM |
| KCl | 3 mM to 50 mM |
| $CaCl_2$ | 0.5 mM to 2.5 mM |
| $KH_2PO_4$ | 0.7 mM to 1.3 mM |
| $MgSO_4$ | 0.9 mM to 4.8 mM |
| $NaHCO_3$ | 15 mM to 35 mM |
| Glucose | 1.0 mM to 50 mM |

Other solutions may be used as a base to form the solutions of the invention. An example of such solution is the solution known as the University of Wisconsin (UW) solution.

The preservation solutions should contain from about 2.5 µM to about 10 µM of cyclosporin per liter of solution, preferably from about 5.0 µM to about 8.0 µM of cyclosporin per liter of solution.

In a preferred procedure of the invention, the donor is treated with the preservation solution while the heart is being harvested. Once isolated and cooled, the heart is put into a plastic bag that is placed into a 4° C.-6° C. water bath. A UW solution with $10^{-5}$ mole per liter concentration of cyclosporin is used for the initial flush and the heart is cooled. During the 18 or 24 hours of preservation, the same solution is perfused through the heart circulating at 1 ml per minute throughout the preservation period. When reperfusion was started a stage reperfusion is used so that 25% of perfusion pressure is introduced for 5-10 minutes, 50% perfusion pressure for 5-10 minutes and 75% perfusion pressure for another 5-10 minutes and finally 100%.

To show the effectiveness of the preservation solutions of this invention, experiments were performed on mongrel dogs (20-26 Kg). Eighty animals served as heart donors and 80 as heterotopic recipients for various experimental groups. Donor and recipient were anesthetized with sodium pentobarbital (30 mg/Kg), incubated, and mechanically ventilated (Puritan-Bennett Companion 2800 Volume Ventilator, Boulder, Colo. 80301). The hearts of the donor animals were exposed through a midline thoracotomy incision. Following heparinization (3 mg/Kg), hypothermic crystalloid cardioplegia was introduced and the heart temperature reduced and maintained at 10° C. Myocardial temperature was monitored by a septal needle thermistor (Electromedic, Inc., TM 2100; Englewood, Colo. 80112). The donor heart was then flushed with approximately 1 liter of the preservation solution in which it would be stored throughout the period of preservation. A UW solution was used for preservation and modified for the various experimental groups. The heart was then excised and placed in a double walled plastic bag containing approximately 100 ml of the UW solution. In those experiments in which a slow constant perfusion (1 ml/min) of the preservation solution was maintained, the innominate artery was cannulated for the perfusion and the effluent was removed via the cannulated pulmonary artery. Approximately 1100 ml was perfused during the 18 hours of preservation. During the preservation period the plastic bag containing the heart was submerged in a cold water bath that maintained the heart temperature at 4.5° C.

As shown in FIG. 1, after preservation, the aorta 18 and pulmonary artery 22 of the donor was connected via the cannula assembly to the left carotid artery 16 and right jugular vein 14 of the recipient animal respectively. The heart was wrapped in a warming pad 32 and myocardial septal temperature was slowly increased by staged reperfusion of arterial blood until defibrillation of the recipient heart was possible at a temperature of approximately 34-35° C. The warming process required 20-30 minutes. The femoral artery 36 and vein 34 of the recipient were isolated and connected by way of an elevated bag having a vent 12 to the left atrium 28 of the donor heart to maintain left atrium pressure at approximately 15 mmHg. Functional changes in the left ventricle (LV) were determined from end systolic elastance (Ees) derived from the pressure/diameter loops recorded from a LV pressure (Millar transducer tipped catheter placed via the apex) and LV-AP diameter measured using sonomicrometery 24 techniques (Triton Technology, Inc., San Diego, Calif.). The heterotopic donor heart functions normally with left atrium pressure maintained at approximately 15 mmHg. Coronary arterial flow was supplied by the recipient's left carotid artery and coronary venous outflow was via the donor heart's pulmonary artery into the recipient's jugular vein. When pressure-diameter loops were measured, flow through the donor heart was altered temporarily by interrupting carotid artery inflow and occluding femoral artery inflow and femoral vein outflow to the left atrium (LA) pressure bag. The LV ventricular output was temporarily directed into the jugular vein. A transducer tip catheter 26 is provided. The dynamic decrease in LA pressure created reductions in LV pressure and LV-AP diameter creating pressure-diameter loops for derivation of Ees. Normal flow patterns were restored following the function measurements. Ees was calculated using Acquire software for data collection (Bowman Cray School of Medicine, Winston-Salem, N.C.) and Spectrum software for data analyses (Bowman Gray School of Medicine, Winston-Salem, N.C.).

The degree of myocardial substrate uptake of the donor heart was determined from blood samples simultaneously collected of coronary venous and arterial blood. Coronary blood flow was determined by measuring coronary venous outflow from the pulmonary artery cannula with a graduated test tube and stopwatch. The levels of glucose, lactate, and pyruvate were determined enzymatically (Sigma Chemical Co., St. Louis, Mo.). Free fatty acids were determined by the Wako NEFA test kit (Wako Chemicals USA, Dallas, Tex.). Oxygen was measured by blood gas analyses (Instrumentation Laboratory model 1306 pH/blood gas analyzer and Instrumentation Laboratory 482 CO-oximeter, Lexington, Mass.). Arterio-venous differences of glucose, lactate, pyruvate, free fatty acids, and oxygen multiplied by coronary blood flow corrected for wet weight of the heart provided myocardial uptake of these substrates.

Myocardial tissue samples were taken using hand-held Dremel tool fitted with a freshly broken 250 μL glass capillary pipette with a diameter of approximately 2.8 mm. The pipette was cooled in liquid $N_2$ prior to taking the tissue samples for high-energy phosphates. The samples were stored at −80° C. until processing. The samples were freeze dried (Lyph-Lock 18, Labconco, Kansas City, Mo.), and prepared for HPLC. ATP, ADP, AMP, adenosine and CP were determined by reverse phase chromatography using a Supelco Supercosil LC-18-T; 250×4.6 mm; 5 μm column. See, F. S. Anderson, et al., "Isocratic separation of some purine nucleotide, nucleoside, and base metabolites from biological extracts by high performance liquid chromatography," *J. Chromotogy*, 121:251-262, 1976.

Biopsy samples were taken by removing a 100-150 mg core of the anterior free wall. The tissue core was made by inserting a freshly scored and broken 100 μl or 250 μl glass micropipette tip into a hand held Dremel Tool drill. This created an extremely sharp coring tool, circularly propelled for sampling the LV muscle tissue for electron microscopy (100 μl) or morphological techniques (250 μl). A purse-string suture closed the hole. The samples for electron microscopy were fixed in 3% glutaraldehyde in 0.1 M cacocylate buffer at 4° C. (pH 7.4). Samples for apoptosis, lamin degradation and PARP fragmentation were immediately frozen in liquid $N_2$ and stored at −80° C. until further use.

Small tissue samples were embedded in Epon following routine embedding procedures. Ultrathin sections were prepared, stained with uranyl acetate and lead citrate and viewed and photographed in a Philips CM 10 electron microscope. Following a semi-quantitative evaluation technique, the biopsies were evaluated to determine the degree of ischemic injury.

The ApoTag in situ apoptosis detection Kit (Amersham) was used to detect apoptotic cells. Visualization of apoptotic cells was done using an anti-digoidgenin antibody conjugated with fluoro-isothiocyanate (FITC) and sections were viewed in a confocal laser microscope (Leica). One negative control section for each tissue sample was prepared and incubated in the absence of the TdT enzyme. For a positive control, the sections were digested with 1 μg DNase-I/ml DNase buffer (Sigma) for 10 min.

Samples of deep-frozen (−80° C.) tissue were mounted with TissueTEK® (OCT compound) on a metal block. Sections 5 μm thick were cut with a cryostat CM 3000 (Leica), put on gelatine-covered glass slides and air dried followed by fixation in acetone for 15 minutes at minus 20° C. The sections were rinsed in PBS and incubated with mouse-antilamin B antibody (Calbiochem, dilution 1:10). After repeated rinsing the sections were incubated in biotin-SP-conjugated-affinipure donkey antimouse IgG Packson ImmunoResearch Inc., dilution of 1:50). Cy 2-streptavidin, (Rockland, dilution 1:100) was followed by nuclear staining with either propidium-iodide or DAPPI (Molecular Probes). Sections were mounted with Mowiol (Hoechst A. G.). They were cover-slipped and viewed in a confocal laser microscope (Leica) or in a DM microscope equipped for fluorescence (Leica). Documentation was carried out on professional Kodak Ektachrome 100 HC film for color slides. All reproductions were made from slides. The number of apoptotic nuclei in myocytes was counted in the microscope and expressed as percentage of the total number of myocytes (a total of 100,000 myocytes and a corresponding number of interstitial cells were examined per sample). Cardiomyocyte nuclei positive for lamin were counted and calculated similarly.

EXPERIMENT

A preservation solution containing Cyclosporine A was used to block apoptosis. Apoptosis is blocked by preventing the activation of the capases.

In the groups in which Cyclosporine A solution was administered, the donor animals were treated with 10 mg/Kg by slow infusion over 45-60 minutes so as not to severely lower the arterial blood pressure which has been shown to be related to the Cyclosporine A vehicle, cremophor. After the donor hearts were isolated, they were exposed to Cyclosporine A ($10^{-5}$ mol/l) by slow perfusion (1.0 ml/min). After preservation, the hearts were heterotopically connected to the recipient and a slow infusion of Cyclosporine A was initiated into the recipient (2.5 mg/Kg) at a rate sufficiently slow so as not to depress the arterial blood pressure of the recipient. The depressed arterial blood pressure was a consistent observation when administering Cyclosporine A acutely in the dog model and may be related to its vehicle, cremophor.

An eighteen-hour period of preservation was used to delineate the appearance of PARP fragments, lamin B, apoptosis and necrosis since 12 hours was considered to be the limit for full functional recovery of stored hearts. Following preservation, the hearts were monitored for 6 hours. Hemodynamic parameters for function were taken every hour during the 6-hour recovery period. Metabolic and histological samples were taken from the donor hearts before preservation, after the preservation, and at 2 and 6 hours during recovery. There were five experimental groups: 1) Group I was a control group with donor hearts removed and immediately reanimated (no preservation) n=10 experiments), 2) Group 11 was 18-hour preservation with slow perfusion of the UW solution (n=12 experiments), 3) Group III was 18-hour preservation with slow perfusion of UW solution with Cyclosporine A (n=8 experiments), 4) Group IV was 24-hour preservation with slow perfusion of the UW solution (n 5 experiments) and 5) Group V was 24-hour preservation with slow perfusion of the UW solution with Cyclosporine A (n=5 experiments).

The data were expressed as means±SEM of at least three independent experiments. The tests used were Student's t-test, ANOVA, Kruskal-Wallis-test, Friedman-test as well as subsequent multiple comparisons by Dunn, Student-Newman-Keuls and Bonferroni. Values of $p<0.05$ were considered to be significant. In all cases, n values correspond to the number of animals.

Figure 2:
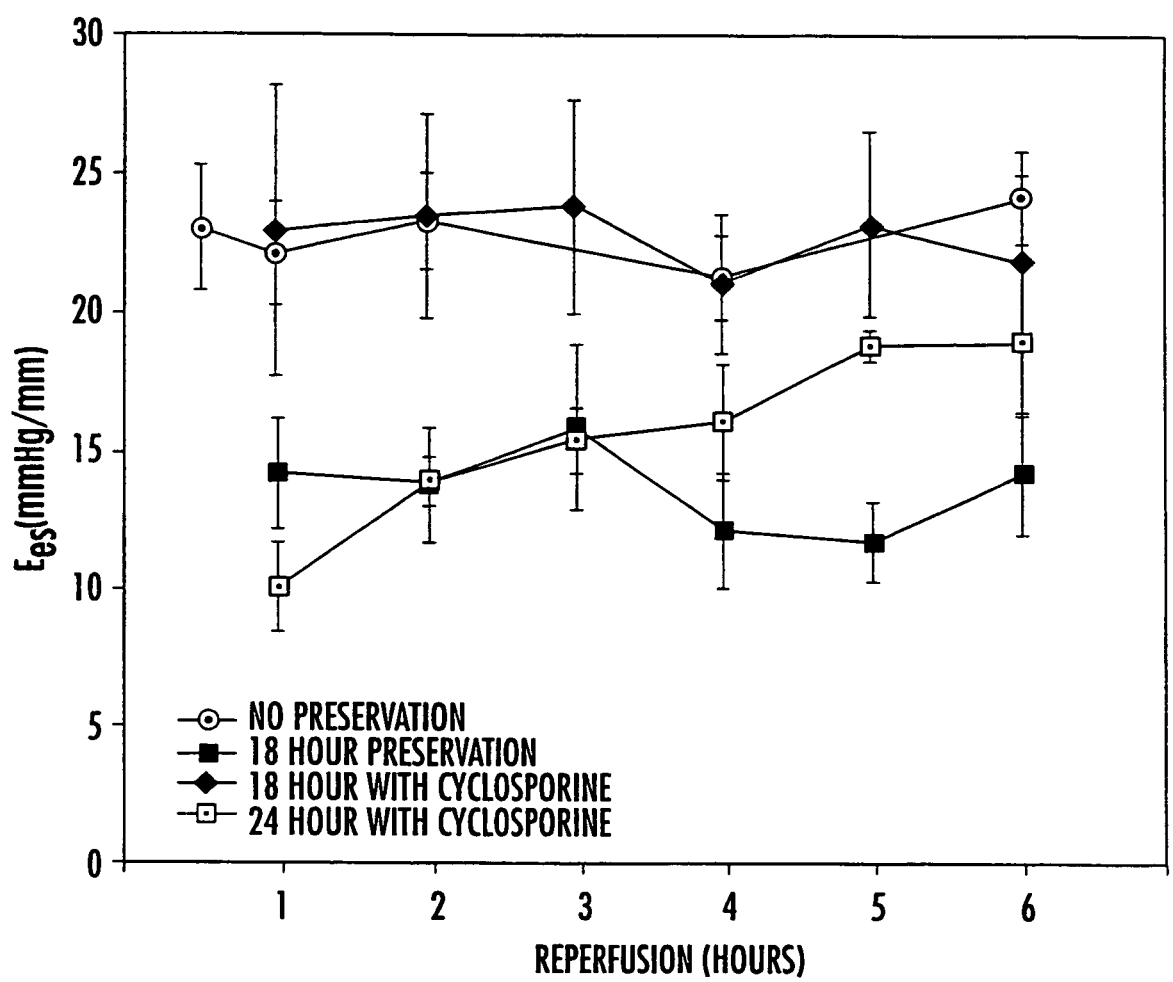
FIG. 2 shows the changes in LV function (Ees) with and without Cyclosporine A treatment for 18 and 24 hours of hypothermic preservation.

The results are shown in FIGS. 2-7. Functional recovery for 18 and 24 hour preservation is shown in FIG. 2. After 18 hours of preservation with no Cyclosporine A, functional recovery was approximately 55-60% after 6 hours of reperfusion. After Cyclosporine A treatment during the 18 hours of preservation, function returned to 100% within 60 minutes and remained at this level throughout the recovery period. There was no functional recovery after 24 hours of preservation without Cyclosporine A. However, treatment with Cyclosporine A during the 24 hour preservation period resulted in functional recovery that was not significantly different with control at 4, 5, and 6 hours during reperfusion.

Figure 3:
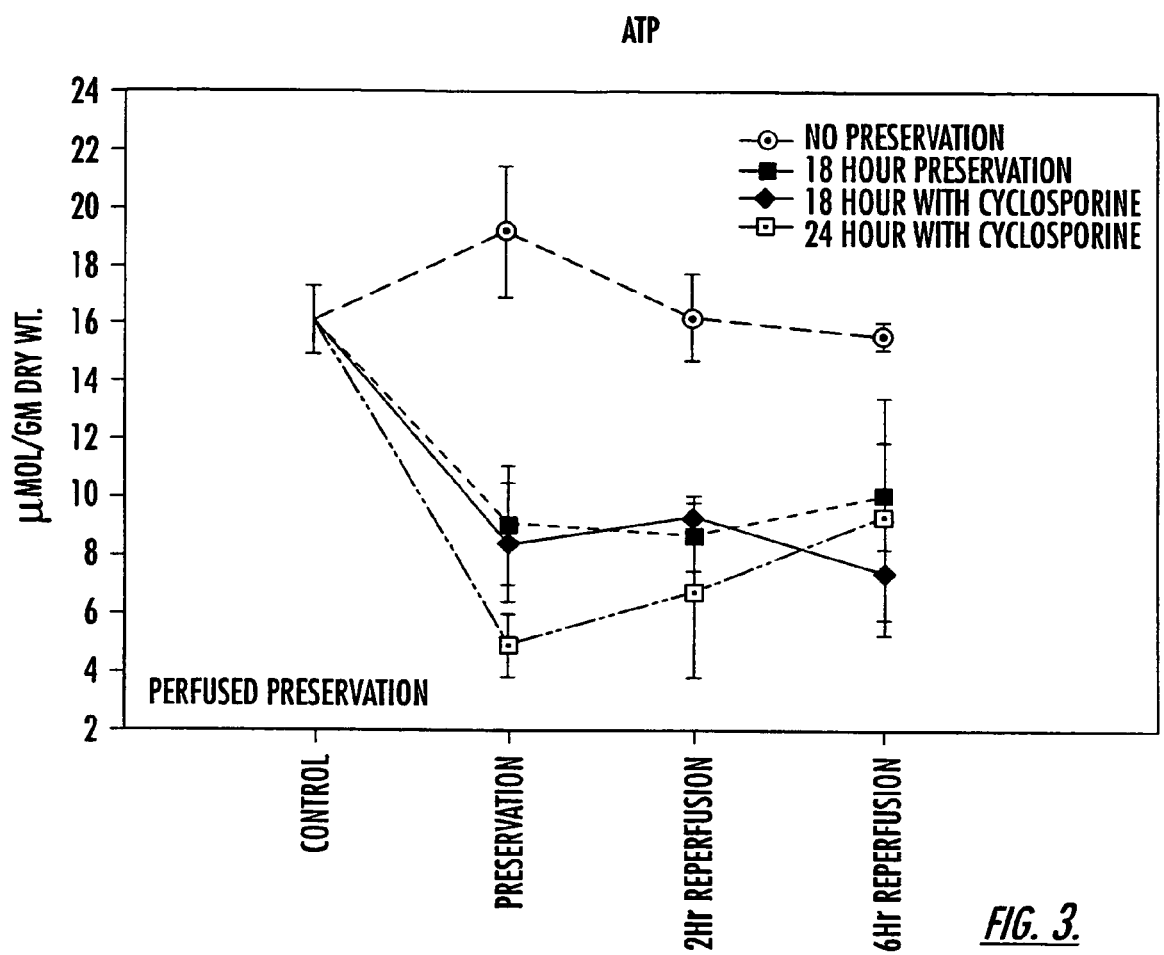
FIG. 3 shows alterations in myocardial ATP concentrations during 6 hours of reperfusion after 18 and 24 hours of preservation with and without Cyclosporine A.
Figure 4:
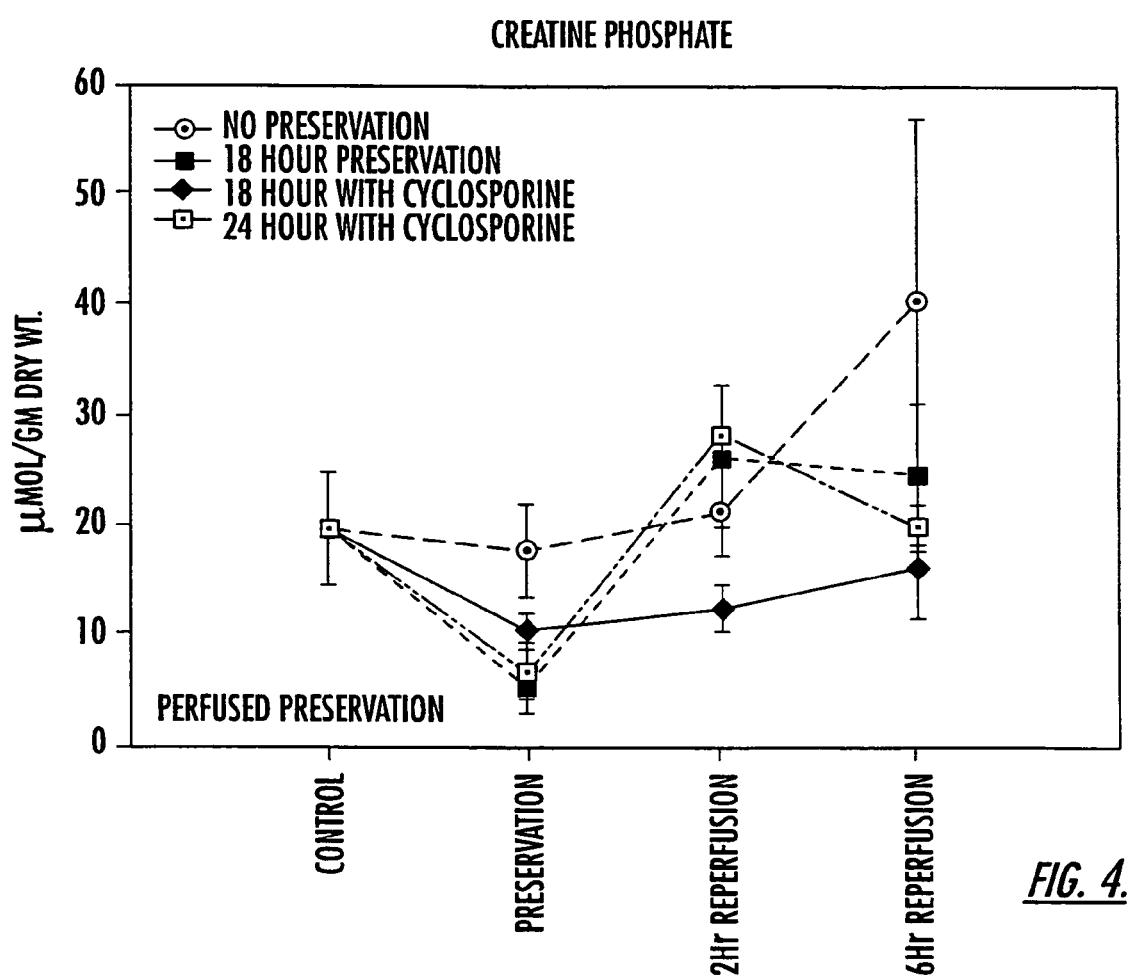
FIG. 4 illustrates the effects on myocardial CP concentration during 6 hours of reperfusion after 18 and 24 hours of preservation with and without Cyclosporine A.
Figure 5:
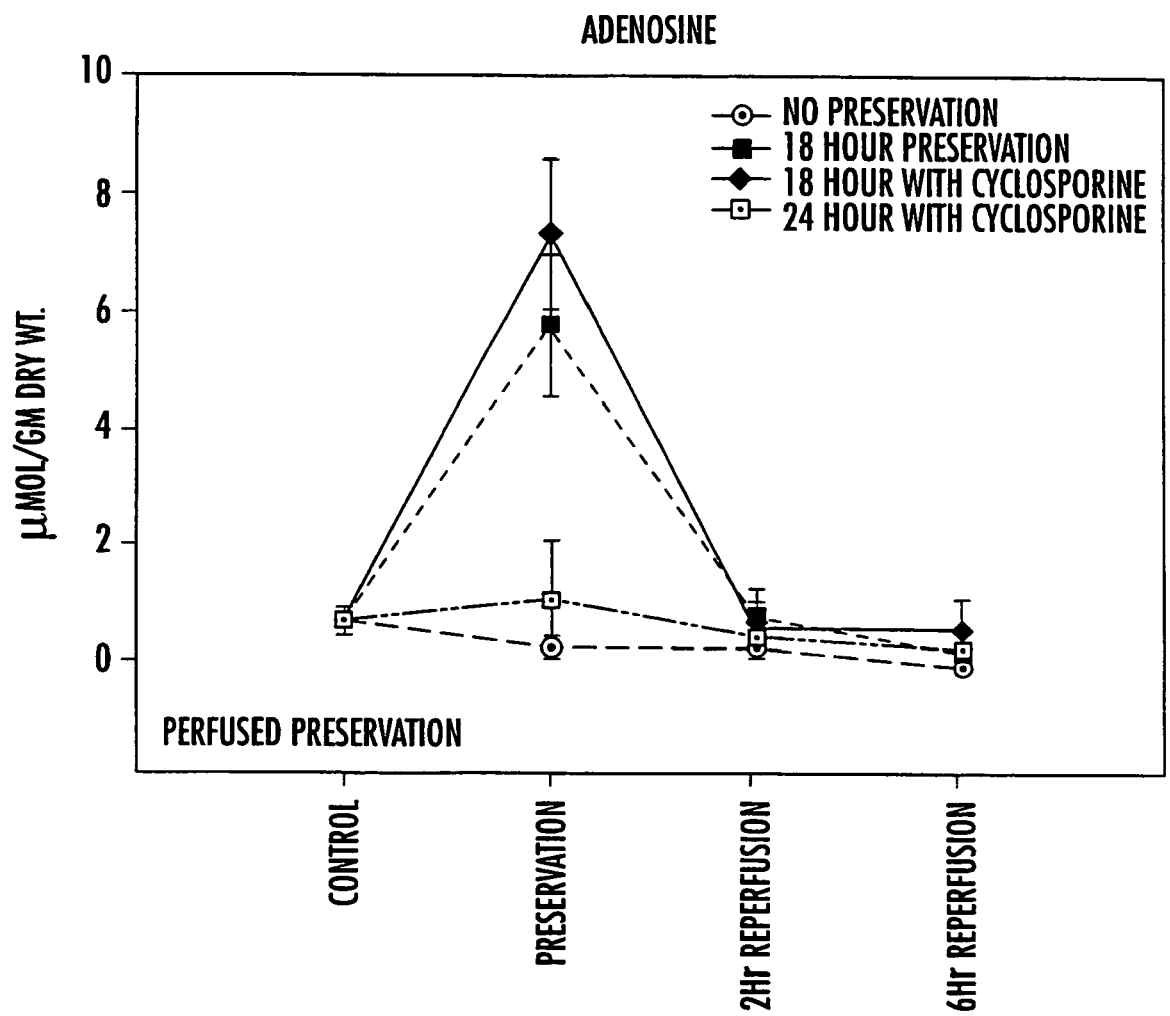
FIG. 5 illustrates the effects of 18 and 24 hours of preservation with and without Cyclosporine A on myocardial adenosine levels during 6 hours of reperfusion.

As shown in FIG. 3, ATP levels were significantly reduced during preservation with and without Cyclosporine A and increased throughout reperfusion although not to significant levels. There was a 66.2% reduction in CP (FIG. 4) during preservation without Cyclosporine A and an 80.0% reduction with treatment. During reperfusion CP returned to control levels. In FIG. 5 there is shown concomitant with the reductions in ATP and CP, adenosine was markedly elevated during preservation and returned to preisolation levels during reperfusion.

Figure 6A:
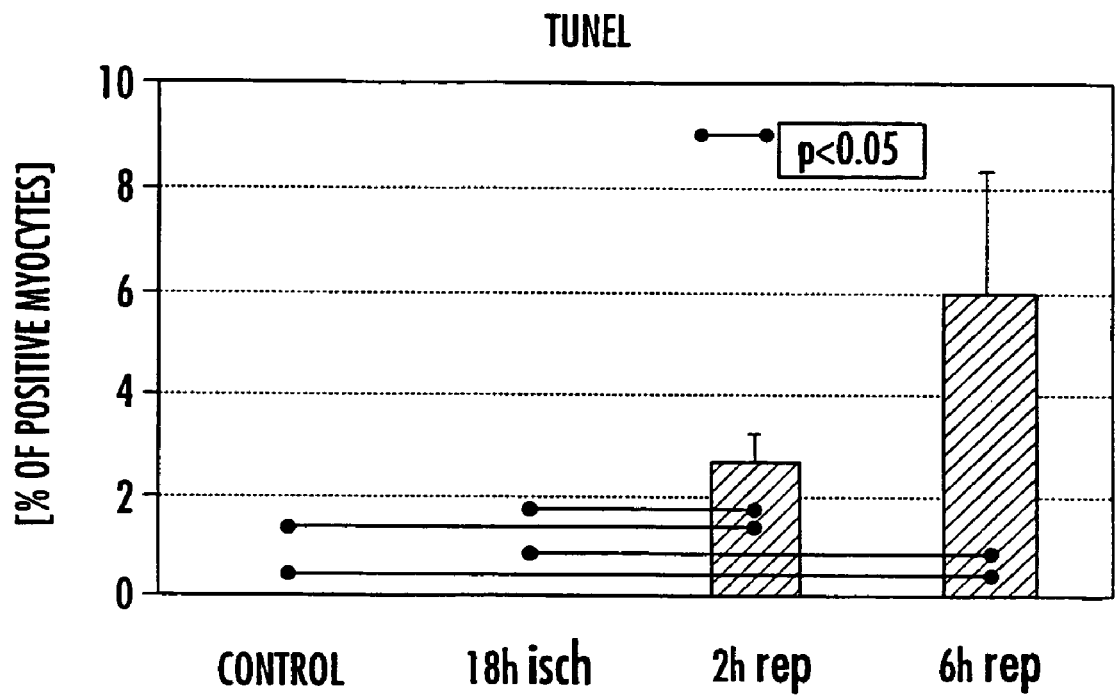
FIG. 6A shows the results of TUNEL for the presence of apoptotic myocytes during 6 hours of reperfusion after 18 hours of preservation with UW solution without Cyclosporine A.
Figure 6B:
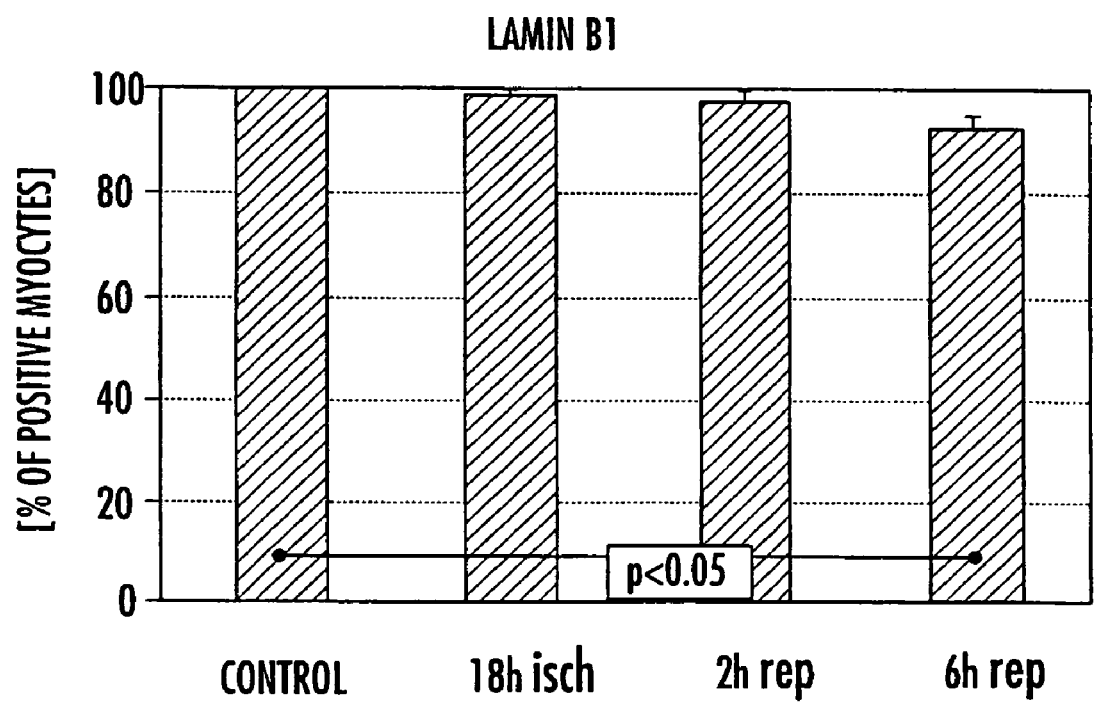
FIG. 6B shows the percent of Lamin $B_1$ reduced from myocardial nuclei under the same experimental conditions.
Figure 7A:
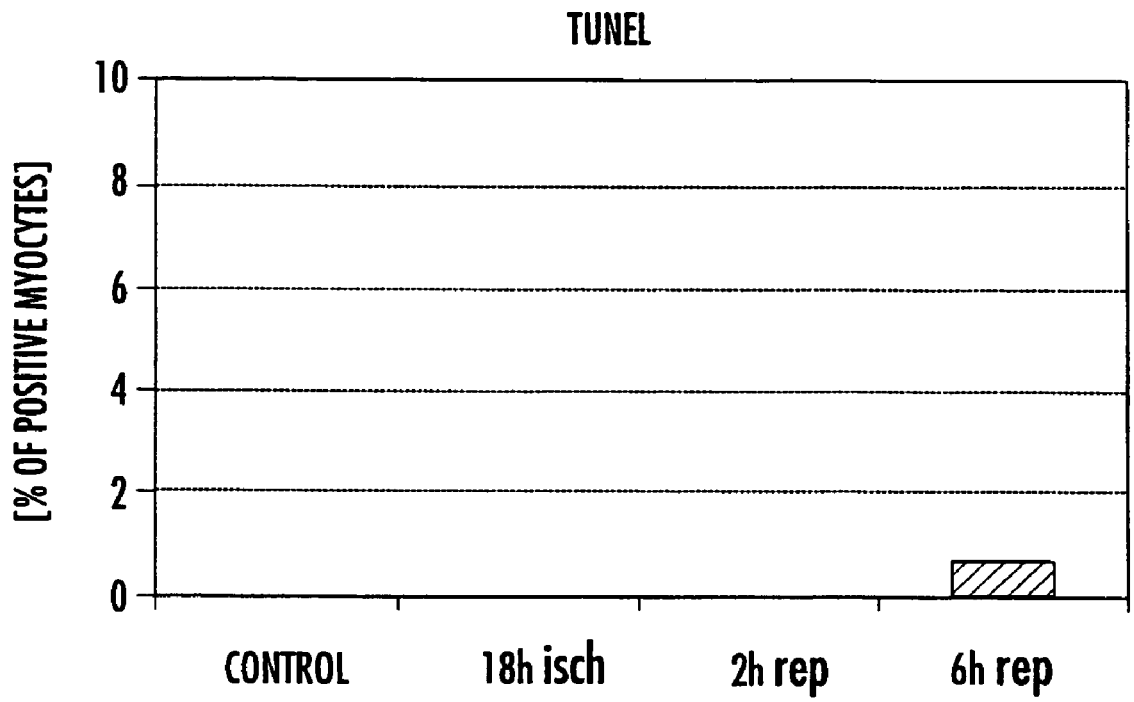
FIG. 7A shows the results of TUNEL during 6 hours of reperfusion after 18 hours of preservation with UW solution and Cyclosporine A.
Figure 7B:
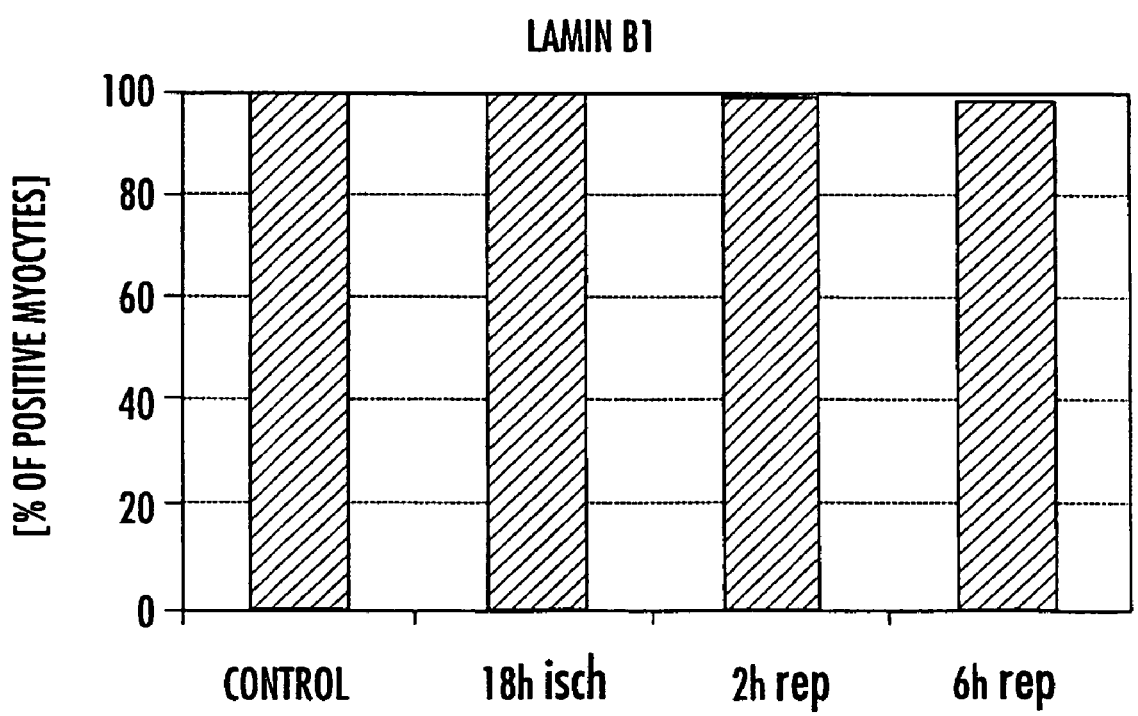
FIG. 7B shows that the percent of Lamin $B_1$ is unchanged in the myocardial nuclei during the reperfusion when Cyclosporine A was used during preservation.

In FIG. 6A there is shown the changes in apoptotic cells (TUNEL). After 2 and 6 hours of reperfusion with no Cyclosporine A, there was a 2 and 6% increase in apoptotic cells. In FIG. 6B, there is shown the changes in Lamin $B_1$. Lamin $B_1$ was decreased 3 and 8% during the same time periods. The morphological appearance of the apoptotic cells in the accompanying micrograph is shown in green. Lamin $B_1$, is shown as green in the bottom micrograph with the red nuclei indicating a loss of Lamin $B_1$. As shown in FIG. 7A, Cyclosporine A treatment prevented apoptosis (TUNEL) formation in myocytes after 18 hours of preservation. FIG. 7B shows that Lamin $B_1$, remained unchanged.

In a canine heterotopic heart transplant model 50-60% functional recovery returned following 18 hours of PRES with University of Wisconsin solution (UW). Concomitant with functional changes, there were significant increases in apoptotic cells and caspase 3 at 2 and 6 hours of reperfusion with a concomitant decrease in Lamin $B_1$ with no necrotic cells. ATP and CP concentrations were reduced during hypothermic preservation (PRES). ATP increased but remained below control during 6 hours of reperfusion while CP returned to levels above control. These results suggested that blockade of apoptosis may prolong myocardial viability during PRES and reperfusion.

Donor hearts were subjected to 18 and 24 hours of PRES (2-4° C.) with and without a preservation solution containing Cyclosporine A treatment (apoptosis blacker). The preservation solution was given to the donor animal (10 mg/kg), in the PRES solution ($10^{-5}$ mol/l) slowly infused during the PRES period (1 ml/min) and to the recipient animal (2.5 mg/kg). After 18 hours of PRES with a solution containing Cyclosporine A, function returned to 100% within 1 hour and stayed at this level throughout a 6 hour recovery period. There were no apoptotic myocytes nor caspase 3 activity after 18 hours PRES with the preservation solution contianing Cyclosporine A (CyS) and Lamin B remain at 100% in the nuclei. Twenty-four hours PRES in UW resulted in no functional recovery. However, after CyS treatment, functional recovery returned to 100% after 4 hours of reperfusion. ATP and CP concentrations were surprisingly the same with or without CyS treatment at 18 hours and lower with 24 hours but returned during reper5fusion to 18 PRES levels. The mechanism of action may be associated with the mitochondrial permeability transition (MPT pore via cyclophilin D binding.

LV functional recovery was evaluated with a working preparation. Although non-working models recovered contractile activity, it was only after they were subjected to physiological workloads that a functional deficit was recognized. The presence of apoptosis in various cardiac diseases as well as in the present studies suggest an important relationship of apoptotic damage and myocardial dysfunction with a relatively low concentration of apoptotic myocytes. The greater predilection of apoptosis rather than necrosis during myocardial ischemia suggests significant differences in contractile behavior during apoptotic versus necrotic myocardial damage. Although functional recovery after 18 hours of preservation without Cyclosporine A reached a plateau, apoptotic damage continued to increase (2% at 2 hrs and 6% at 6 hrs). However, the escalating appearance of apoptotic damage within the cells may indicate that apoptotic signals were initiated with intermediate reactions continuing toward DNA fragmentation which require the presence of ATP.

Traditionally, storage techniques for hearts utilize three different procedures; 1) static storage, 2) low perfusion and 3) high perfusion. Static storage is accomplished by flushing the heart allograft with the preservation solution and placing it in a storage bag submerged in ice for the duration of the preservation. With low perfusion the only difference from static storage is that the preservation solution is slowly perfused through the donor heart at flows in the range of 1-1.5 ml/minute or perfusion pressures approximating 5 mmHg. The pulmonary artery effluent is discarded which in the present experiments was approximately 1100 ml. High perfusion techniques differ significantly but suggest greater heart storage times accompanied by greater technical complexity and cost. In the present experiments, a low perfusion was used to deliver the preservation solution to the heart maintained at approximately 4° C. This provided a constant removal of metabolic endproducts and exposure of the heart to nutrients, as stored hearts are very energy dependent.

ATP and CP concentrations were markedly reduced during preservation with Cyclosporine A and without. The levels were lower after 24 hours than at 18 hours and upon reperfusion ATP levels were only 55-60% of control after 6 hours while CP levels returned to normal. Although temperatures at 2-4° C. slow metabolism by nearly 90%, mitochondrial function continues. Slower functional recovery after 24 hours of preservation with Cyclosporine A may suggest that measures to enhance ATP levels concomitant with apoptosis blockade may provide greater levels of myocardial protection.

Apoptosis was found to be an important cell mediator for attenuating functional recovery. Eighteen hours of preservation with UW solution resulted in only 50-60% functional recovery with significant amounts of apoptotic cells in the myocardium. with no necrotic cells. Blocking apoptosis with Cyclosporine A resulted as the prolongation of viability to 18 and 24 hours and may provide a successful method for extending heart preservation.

The possible mechanism for the action of Cyclosporine A in providing additional protection may be mediated by the MTP pore. Under conditions of oxidative stress and $Ca^{++}$ overload within the mitochondria, the MTP pore opens, resulting in volume imbalance from the hyperosmolality of the mitochondria matrix. This will ultimately cause membrane rupture and release of caspase-activating protein and the uncoupling of oxidative phosphorylation and disruption of ATP synthesis precipitating apoptosis and necrosis respectively. The results support ATP conservation, but also suggest that Cyclosporine A may be more important in preventing apoptosis via MPT pore stabilization thereby conserving myocytes and functional integrity. The mechanism of action for Cyclosporine A on MPT pore stabilization is by the binding of cyclophilin D. Therefore, a central role for MPT pore formation and its stabilization by Cyclosporine A acts to attenuate both apoptotic and necrotic cellular processes and merits important consideration in organ preservation.

The results suggest that treatment with a preservation solution containing Cyclosporine A during preservation is beneficial in preventing ATP loss, inhibiting both apoptosis and necrosis and extend this preservation barrier. In summary, use of cyclosporin in a preservation solution prolongs myocardial viability during donor heart preservation.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for blocking apoptosis during preserving and storing a heart awaiting transplantation comprising:
   perfusing said heart for up to 24 hours with a solution consisting essentially of:
   (a) a balanced isotonic solution in a physiologically acceptable amount;
   (b) cyclosporin A in an amount from about 2.5 µM to about 10 µM per liter of solution; and
   (c) water.

2. The method according to claim 1 wherein said balanced isotonic solution includes sodium, potassium, calcium, magnesium ions and bicarbonate.

3. The method according to claim 1 wherein said cyclosporin A is present in an amount from about 5.0 µM to about 8.0 µM per liter of solution.

4. The method according to claim 1 wherein said balanced isotonic solution comprises:

| Concentration Ranges in 1 Liter | |
| --- | --- |
| NaCl | 85 mM to 145 mM |
| KCl | 3 mM to 50 mM |
| $CaCl_2$ | 0.5 mM to 2.5 mM |
| $KH_2PO_4$ | 0.7 mM to 1.3 mM |
| $MgSO_4$ | 0.9 mM to 4.8 mM |
| $NaHCO_3$ | 15 mM to 35 mM |
| Glucose | 1.0 mM to 50 mM. |

5. A medicament for preserving and storing a heart while awaiting transplantation consisting essentially of:
   (a) a balanced isotonic solution in a physiologically acceptable amount;
   (b) cyclosporin A in an amount from about 2.5 µM to about 10 µM per liter of solution; and
   (c) the remaining being water,
whereby said heart awaiting transplantation is preserved for up to 24 hours.

6. The medicament according to claim 5 wherein said balanced isotonic solution includes sodium, potassium, calcium, magnesium ions and bicarbonate.

7. The medicament according to claim 5 wherein said cyclosporin A is present in an amount from about 5.0 µM to about 8.0 µM per liter of solution.

8. The medicament according to claim 5 wherein said balanced isotonic solution comprises:

| Concentration Ranges in 1 Liter | |
| --- | --- |
| NaCl | 85 mM to 145 mM |
| KCl | 3 mM to 50 mM |
| $CaCl_2$ | 0.5 mM to 2.5 mM |
| $KH_2PO_4$ | 0.7 mM to 1.3 mM |
| $MgSO_4$ | 0.9 mM to 4.8 mM |
| $NaHCO_3$ | 15 mM to 35 mM |
| Glucose | 1.0 mM to 50 mM. |

* * * * *